United States Patent
Bensen

(10) Patent No.: US 6,677,859 B1
(45) Date of Patent: Jan. 13, 2004

(54) METHOD AND APPARATUS FOR DETECTING A FLUID AND A TEMPERATURE

(75) Inventor: Bent Thorning Bensen, Elsinore (DK)

(73) Assignee: Bent Thorning Bensen A/S, Elsinore (DK)

(*) Notice: Subject to any disclaimer, the term of this patent is extended or adjusted under 35 U.S.C. 154(b) by 0 days.

(21) Appl. No.: 09/598,842

(22) Filed: Jun. 21, 2000

Related U.S. Application Data

(63) Continuation of application No. PCT/DK98/00577, filed on Dec. 22, 1998.

(30) Foreign Application Priority Data

Dec. 22, 1997 (DK) .............................................. 1511/97

(51) Int. Cl.⁷ .............................................. G08B 21/00
(52) U.S. Cl. ..................... 340/604; 340/605; 340/572.1; 340/573.1; 340/627; 340/552; 340/568.1
(58) Field of Search ................................ 340/604, 605, 340/572.1, 573, 627, 552, 568.2

(56) References Cited

U.S. PATENT DOCUMENTS

| | | | | |
|---|---|---|---|---|
| 3,949,388 A | * | 4/1976 | Fuller ..................... | 340/189 M |
| 4,646,066 A | | 2/1987 | Baughman et al. ......... | 340/540 |
| 4,653,491 A | * | 3/1987 | Okada et al. ............ | 128/138 A |
| 4,792,790 A | | 12/1988 | Reeb ........................... | 340/572 |
| 4,800,370 A | * | 1/1989 | Vetecnik ..................... | 340/573 |
| 5,091,704 A | * | 2/1992 | Kopera ........................ | 331/65 |
| 5,266,928 A | * | 11/1993 | Johnson ...................... | 340/604 |
| 5,291,180 A | | 3/1994 | Reeb ........................... | 340/572 |
| 5,463,377 A | * | 10/1995 | Kronberg .................... | 340/605 |
| 5,570,082 A | * | 10/1996 | Mahgerefteh et al. ...... | 340/604 |
| 5,986,549 A | * | 11/1999 | Teodorescu ................. | 340/561 |
| 6,097,297 A | * | 8/2000 | Fard ............................ | 340/604 |
| 6,107,924 A | * | 8/2000 | Kasai et al. ................ | 340/627 |

FOREIGN PATENT DOCUMENTS

| | | | | |
|---|---|---|---|---|
| EP | 0715152 B1 | 11/1999 | ......... | G01D/27/02 |
| GB | 2113835 A | 8/1983 | ............ | G01B/7/00 |
| WO | WO 99/08245 | 2/1999 | ......... | G08B/13/24 |
| WO | WO 99/33037 | 7/1999 | ......... | G08B/21/00 |

* cited by examiner

*Primary Examiner*—Daniel J. Wu
*Assistant Examiner*—Tai T. Nguyen
(74) *Attorney, Agent, or Firm*—Darby & Darby

(57) ABSTRACT

A method and apparatus for detecting a fluid; said method comprising providing one or more oscillators transmitting electromagnetic energy; providing one or more resonant circuits receiving electromagnetic energy from the oscillators; bringing the fluid and the one or more resonant circuits into contact with each other so that the receptions of electromagnetic energy of the resonant circuits are changed; and detecting changes of the transmissions of the oscillators by changes in one or more characteristics thereof upon the changes in the receptions of the electromagnetic energy of the resonant circuits; and use thereof for the detection of fluid levels, empty containers, and leak of fluids from containers and bodies containing said fluids; e.g. for monitoring collection of drain fluid from a human or for monitoring leak of fluid from a human suffering from urinary and/or fecal incontinence. Further, a method and apparatus for detecting a temperature, and sensing devices for sensing an external parameter, in particular a fluid or a temperature.

17 Claims, 17 Drawing Sheets

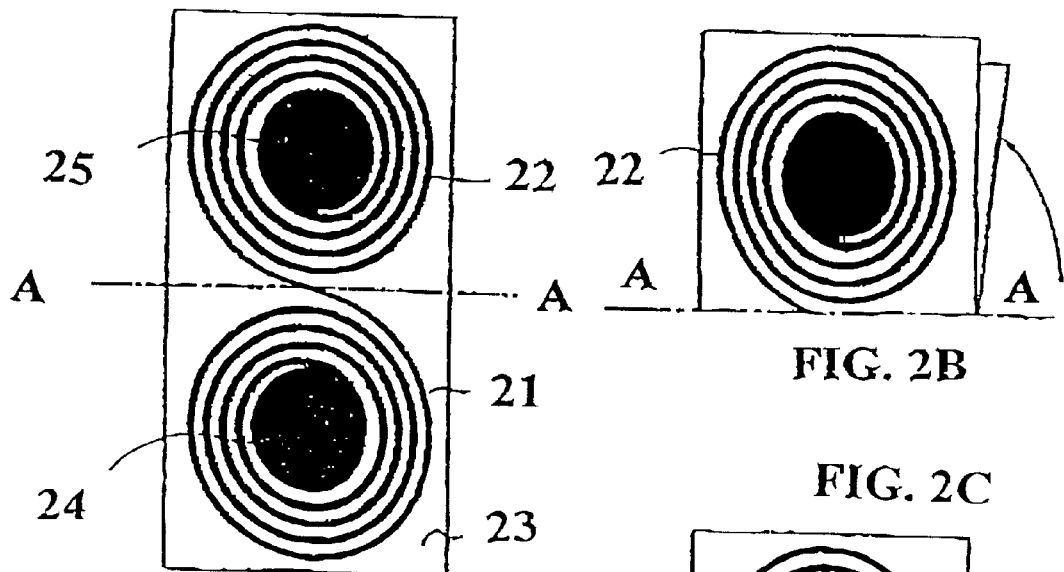
FIG. 2A
FIG. 2B
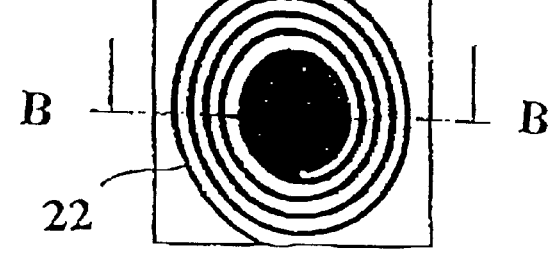
FIG. 2C
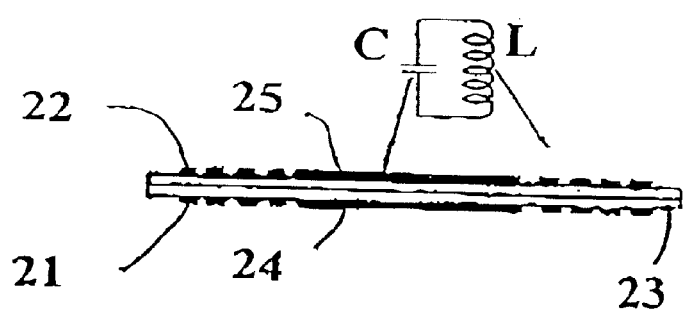
FIG. 2D

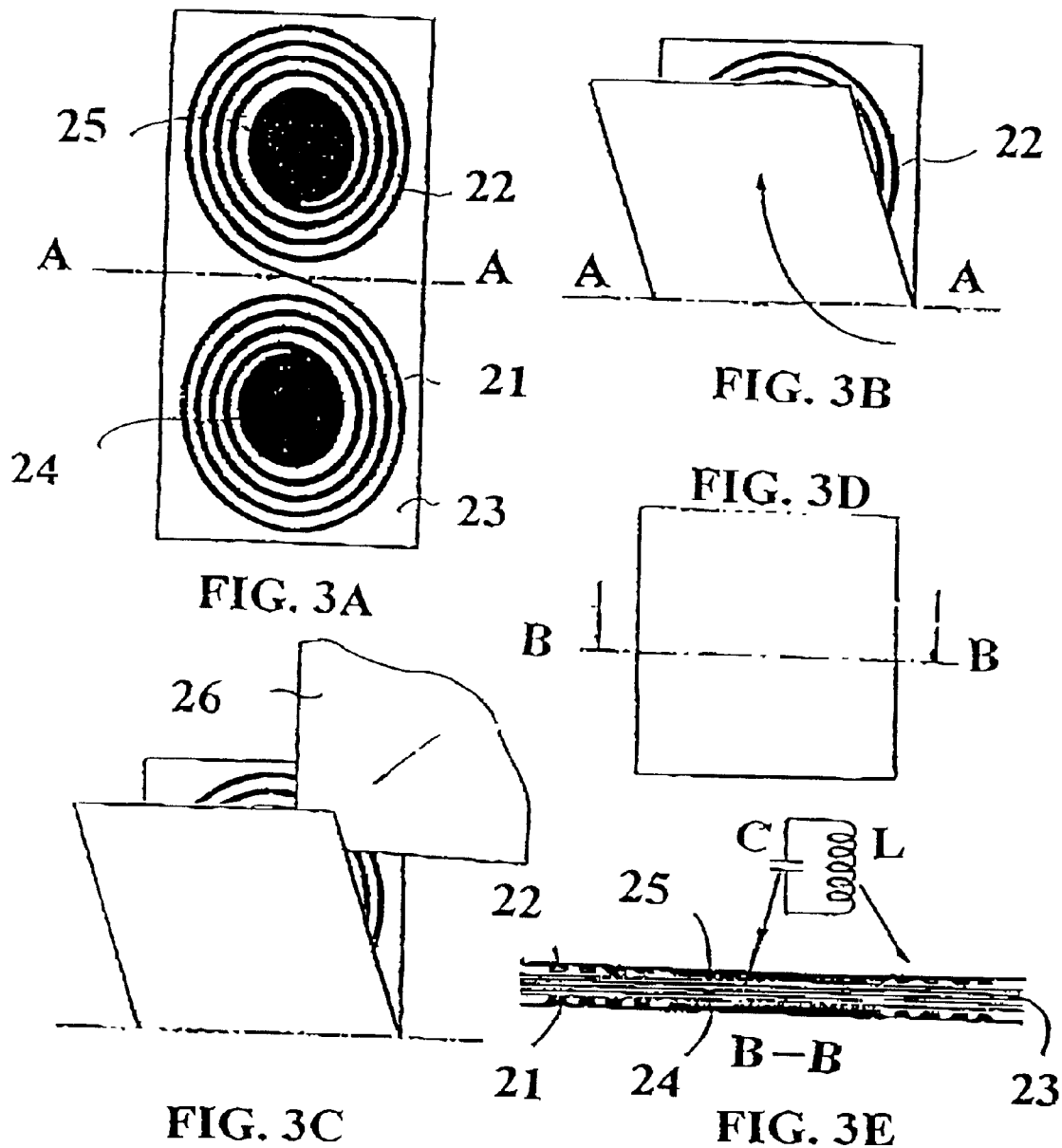

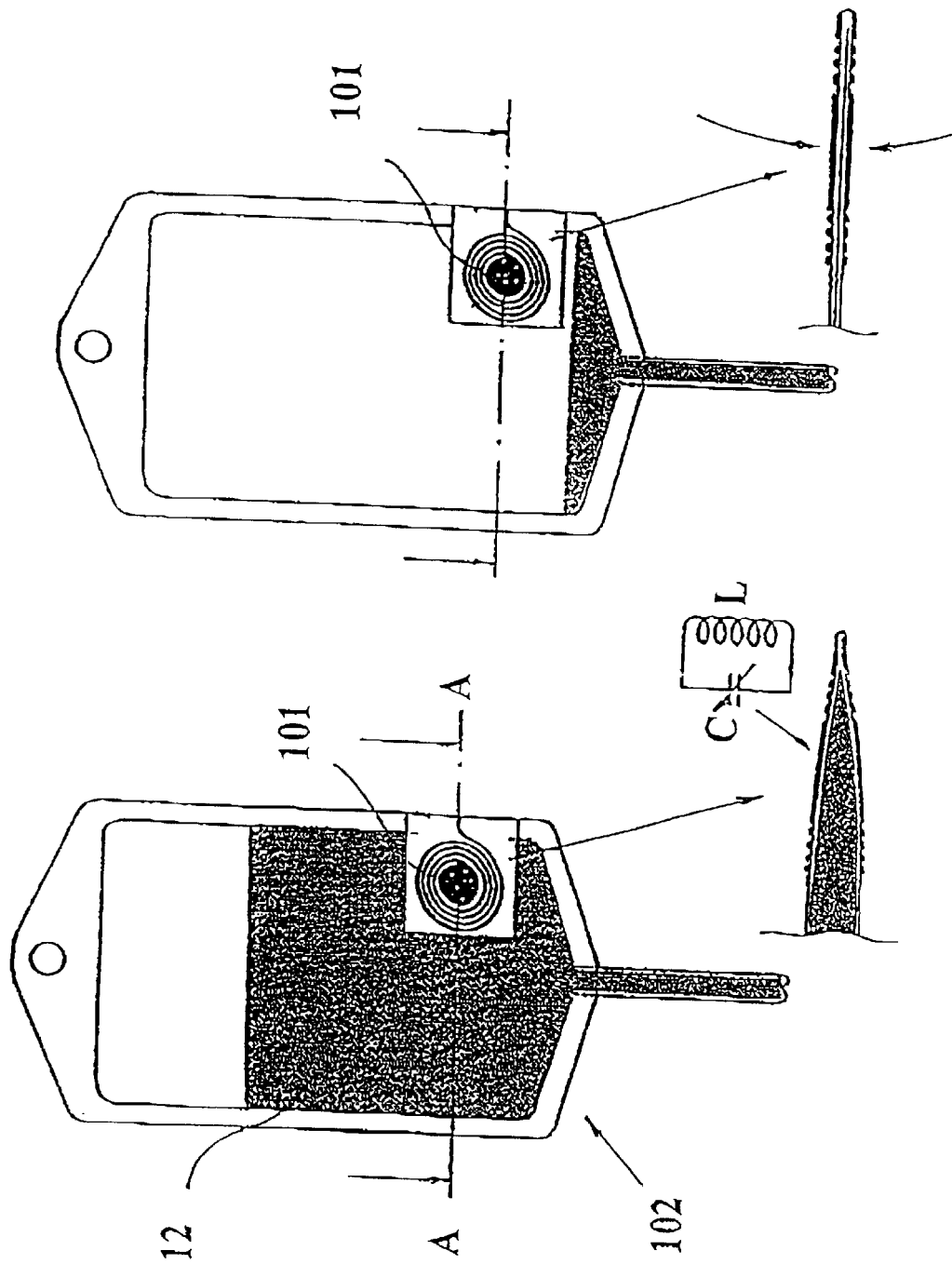

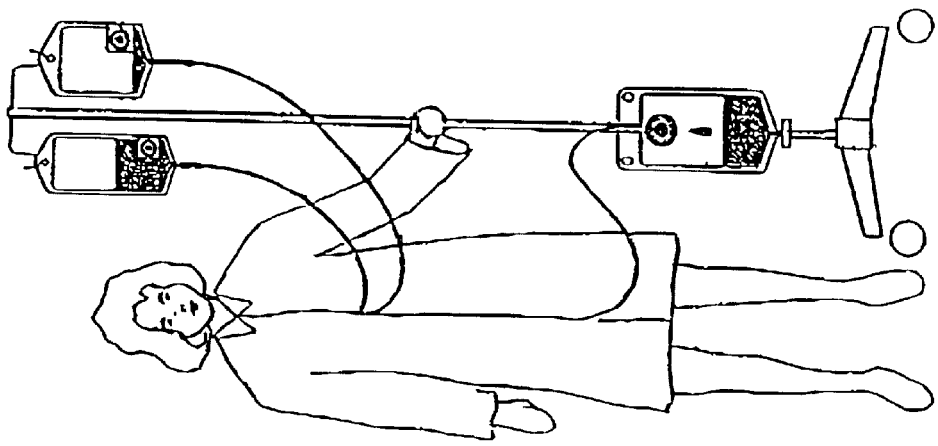
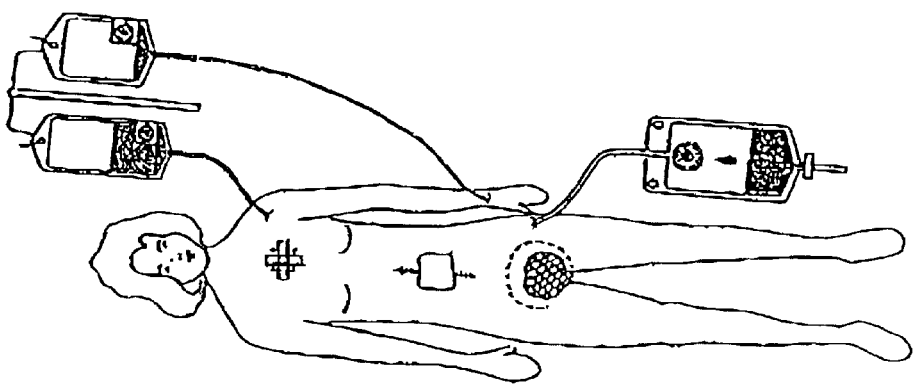
FIG. 12 B
FIG. 12 A

METHOD AND APPARATUS FOR DETECTING A FLUID AND A TEMPERATURE This is a continuation of international application Ser. No. PCT/DK98/00577 filed Dec. 22, 1998, the entire disclosure of which is incorporated herein by reference.

BACKGROUND OF THE INVENTION

The present invention relates to a method and apparatus for detecting a fluid; use thereof for detecting the level of fluid in a container; and use thereof for monitoring a leak of fluid from a body containing said fluid, in particular a leak of body fluid from a human or an animal.

The present invention further relates to a method and apparatus for detecting a temperature.

The present invention still further relates to a sensing device for sensing an external parameter, in particular a fluid or a temperature.

1. The Technical Field

Generally detection of a fluid, e.g. for detecting the level of a fluid in a container or for detecting a leak of fluid from a body such as a container or a human or animal body containing said fluid comprises production of a sensor signal of the fluid and detection of the produced sensor signal by appropriate detection electronics.

In applications of e.g. detecting levels or leaks of stationary oil containers, or detecting leak of body fluids from patients or elderly confined to a bed, the sensor of the fluid and the detection electronics are typically interconnected by electrically conducting connectors e.g. wires or cables. However, such connections can be sensitive to damage and for patients or elderly confined to a bed they can be very inconvenient and put severe constrains on their movability.

Particularly for patients or elderly who are able to walk around, such electrical connections cannot be used without restricting their movability.

Since lack of movability of patients and elderly requires an increased level of monitoring of e.g. wounds and urinary and faecal incontinence by personnel, such a monitoring often being considered inconvenient and cumbersome, electrical connections of monitoring devices implicitly contribute to bad sanitary conditions for patients and elderly and contaminated environments of wound healing sections, incontinence sections and the like of hospitals and nursery homes.

A similar situation holds for monitoring the temperature of patients and elderly.

Wireless connection based on suitable receiver/-transmitter electronics at the sensor and detection electronics can be contemplated. However, in order to function, such electronics requires a portable power supply such as a voltage battery. This is impractical because of the necessary exchange or recharge of discharged batteries.

Consequently there is a need for wireless connection of fluid sensor, or temperature sensor, respectively, and detection electronics which do not require portable power supply; as well as sensors suited for sensing exposure of an external parameter, in particular fluid or a temperature without requiring external power supply.

2. Prior Art Disclosures

International Application No. PCT/NL/00083 discloses an assembly for detecting and signalising wetness of a diaper; said assembly comprising an electronic device mounted in a housing to be applied on a diaper and directly connected to connectors on a sensor strip adhered to the inside or outside of said diaper for detecting presence of wetness near said conductors.

U.S. Pat. No. 4,646,066 discloses an indicator device and method of measuring incremental environmental exposure of an environmental parameter; said method comprising measuring responses of a target to an electromagnetic interrogation signal; said target. including a tuned circuit and an element that is sensitive to environmental exposure, especially exposure to specified fluids e.g. liquids and water vapour, influencing the electronic or ionic conductivity. There is no teaching of parameter influences including the capacitance of the tuned circuit, nor of a measuring method based on changes of transmission of electromagnetic energy of oscillators transmitting electromagnetic energy to the tuned circuits.

EP 0 715 152 discloses a sensing device for sensing the presence or absence of an article, e.g. a material, a liquid, a powder, and the human body; said device comprising an oscillator for generating a high frequency signal; a sensor including a resonance circuit for receiving the high frequency signal from the oscillator and a detector for producing a signal relating to a variation of an impedance change of the sensor; said sensor and detector being coupled through a cable.

GB 2 113 835 discloses a sensor for detecting quantities such as position, force, pressure, liquid level, flow, temperature, voltage, current, and magnetic field; said sensor comprising opto-electric means for converting optical energy into electric energy and vice versa and at least one electric resonant circuit and means arranged to influence a characteristic of the resonant circuit by the quantity to be detected.

U.S. Pat. No. 5,570,082 discloses a device for detecting wetness in diapers for the purpose of calling the attention of the caretaker. The device is a combination of an antenna, a non-linear element and two parallel electrodes, the two electrodes being enbedded in the diaper in an area likely to experience wetness and being adapted to provide a strong coupling between the antenna and the non-linear device when subjected to wetness thereby reducing the resistance between the electrodes. This device does not include a resonant circuit.

DISCLOSURE OF THE INVENTION

Object of the Invention

It is an object of the present invention to provide a method and apparatus for detecting a fluid without using an electrical connection between a sensor of the fluid and an electronic detection system therefore and without requiring a portable power supply for the fluid sensor.

It is another object of the present invention to provide a method and apparatus for detecting the level of a fluid in a container, in particular the level of a human body fluid collected in a container; or for detecting the level of an infusion liquid in a container, in particular the level of an infusion liquid in a plastic bag, e.g. of soft plastic that collapses during emptying thereof.

It is another object of the present invention to provide a method and apparatus for detecting a body fluid from a human or animal body, in particular a leak of body fluid from a human suffering from e.g. urinary and/or faecal incontinence, a human or animal undergoing surgery requiring a drain of body fluid, or a human or animal having e.g. a bleeding wound.

It is another object of the present invention to provide a method and apparatus for detecting a temperature.

It is another object of the present invention to provide sensors for such methods and apparatus Further objects will be apparent from the description,

Solution According to the Invention

In an aspect, the present invention relates to a method and an apparatus for detection of a fluid, and use thereof.

"Method of Detecting a Fluid"

In an aspect according to the invention these objects are achieved by providing a method of detecting a fluid as claimed in claim 1; said method comprising providing one or more oscillators transmitting electromagnetic energy; providing one or more resonant circuits receiving electromagnetic energy from the oscillators; bringing the fluid and the one or more resonant circuits into contact with each other so that the receptions of electromagnetic energy of the resonant circuits are changed; and detecting changes of the transmissions of electromagnetic energy of the oscillators by changes in one or more characteristics thereof upon the changes in the receptions of the electromagnetic energy of the resonant circuits, whereby receiver circuits for receiving and detecting responses of the resonant circuits can be avoided.

"Apparatus for Detecting a Fluid"

In another aspect according to the invention these object are further achieved by providing an apparatus as claimed claim 6; said apparatus comprising one or more oscillators for transmitting electro-magnetic energy; one or more resonant circuits for receiving electromagnetic energy from said oscillators; and one or more detectors for detecting changes in one or more characteristics of the one or more oscillators upon changes in characteristics of the resonant circuits by contact thereof with the fluid, whereby a simplified apparatus is obtained which avoids receiver circuits for receiving and detecting responses of the resonant circuits.

According to the invention it surprisingly turns out that electrically conducting connectors between the sensor of the fluid and the detection electronics, and battery power supply of the sensor, and receiver circuits for receiving and detecting responses of resonant circuits of the sensors can be avoided.

This provides a number of advantages e.g. that the sensor of the fluid can be separated from the detection electronics for detecting changes in the sensor. This is particularly advantageous when monitoring bodies containing fluid wherein the sensor and the detection electronics used cannot be connected permanently by electrically conductions connectors, or when they can only be connected by such connectors with great difficulties or inconveniences. Also, the oscillators and detection electronics can be simplified.

"Uses of the Method and Apparatus for Detecting a Fluid"

Accordingly, in still another aspect according to the invention there is provided uses of the method or the apparatus as claimed for detection of fluid level in one or more containers, in particular incontinence containers, specifically diapers; and use for detecting whether a container containing a fluid has been emptied for the fluid in particular emptying of an infusion containing use for monitoring leak of fluid from a container, or a human or animal body, in particular from a human suffering from urinary and/or faecal incontinence; whereby the health care personnel can monitor the hygienic condition of e.g. a diaper. When a body leak has been detected proper care of e.g. changing the diaper can then be taken.

Another aspect of the invention relates to a method and an apparatus for detection of a temperature, or a temperature difference, and use thereof.

"Method of detecting a temperature"

In an aspect according to the invention these objects are achieved by providing a method of detecting a temperature; said method comprising providing one or more oscillators transmitting electromagnetic energy; providing one or more resonant circuits receiving electromagnetic energy from the oscillators; exposing the the one or more resonant circuits to the temperature to be detected so that the receptions of electromagnetic energy of the resonant circuits are changed; and detecting changes of the transmissions of electromagnetic energy of the oscillators by changes in one or more characteristics thereof upon the changes in the receptions of the electromagnetic energy of the resonant circuits, whereby receiver circuits for receiving and detecting responses of the resonant circuits can be avoided.

"Apparatus for Detecting a Temperature"

In another aspect according to the invention these object are further achieved by providing an apparatus; said apparatus comprising one or more oscillators for transmitting electromagnetic energy; one or more resonant circuits for receiving electromagnetic energy from said oscillators; and one or more detectors for detecting changes in one or more characteristics of the one or more oscillators upon changes in characteristics of the resonant circuits by exposure thereof to a temperature, whereby a simplified apparatus is obtained which avoids receiver circuits for receiving and detecting responses of the resonant circuits.

According to the invention it surprisingly turns out that electrically conducting connectors between the sensor of the temperature and the detection electronics, and battery power supply of the sensor, and receiver circuits for receiving and detecting responses of resonant circuits of the,sensors can be avoided.

This provides a number of advantages e.g. that the sensor of the temperature can be separated from the detect on electronics for detecting changes in the sensor. This is particularly advantageous when monitoring bodies for a temperature wherein the sensor and the detection electronics used cannot be connected permanently by electrically conductions connectors, or when they can only be connected by such connectors with great difficulties or inconveniences. Also, the oscillators and detection electronics can be simplified.

"Uses of the Method and Apparatus for Temperature Measurement"

In addition to the use of the fluid detection method and apparatus described above, the present invention additionally provide the use of the method and apparatus as claimed for detection of a temperature.

Temperature sensors comprising temperature sensitive resonant circuits may be designed to change their impedances at predetermined temperatures, typically in the range 35–42° C., preferably 36–40° C., most preferred 36–38° C., particularly about 37° C.

In addition to monitor patients or elderly for leak of body fluid, or supply of fluid to the body, their temperature can be monitored.

"Sensing Devices of External Parameters"

Still another aspect of the present invention relates to sensors usable for such methods and apparatus in sensing external parameters, more specifically it relates to sensing devices comprising resonant circuits which are responsive, to parameters that are able to influence the impedance thereof, e.g. responsive to a fluid or a temperature.

According to an aspect of the invention, there is provided a sensing device said device comprising a substrate having a back side and a front side, and at least one electrical conducting means, comprising an inductance positioned on or embedded in said back side, front side, or both, of the substrate; said substrate further having at least two parts in a mutual overlaying relationship, so that said conducting means together with at least a part of the substrate provide a capacitance; said inductance and capacitance being electrically connected to form a resonant circuit; and said conducting means being exposed to the external parameter to affect a parameter of said resonant circuit, whereby there is provided a resonant circuit which is easy to manufacture, e.g. by mass manufacturing using continuous substrate coating techniques.

In a preferred embodiment, the two folded sides of the substrate are rotatable around the folding axis, whereby it is obtained that the capacitance formed therebetween can be varied. This embodiment is particular useful when the sensing device is tagged to two sides of a container which sides can get closer or further apart depending on the container having a content, e g. fluid or not. An example being a urine collection bag having a sensing device tagged to the edge thereof, the sides of the bag getting further apart as the bag is being filled.

In a preferred embodiment, the sensing device comprises accession means for a fluid to affect the impedance of the resonant circuit thereby making the sensor particularly suited for detecting a fluid.

In another preferred embodiment, the sensing device comprises a temperature sensitive means thereby allowing remote and wireless monitoring of the temperature of e.g. a patient or an elderly.

"Articles Comprising the Sensing Device"

In another aspect of the present invention there is provided an article comprising the sensing device including a transmitter/receiver combination.

Preferred articles include, but are not limited to, articles for containing or for taking up fluid or for delivering fluid; and articles for measuring temperature; such container e.g. being monitored for being filled or being emptied.

In a preferred embodiment, the article consists of an hygienic article for healthy development and maintenance of health.

In a particularly preferred embodiment, the article consists of an absorbent or a bandage in form of a wrap or a trapping used to protect, cover or immobilise an injured or diseased part of a human or an animal, or used during surgery.

In a particularly preferred embodiment, the article consists of an absorbent for urine or facea, in particular diaper.

"Use of Articles Comprising the Sensing Device"

Articles comprising a sensing device according to the present invention are preferably used in a method of monitoring hygienic conditions of one or more patients said method comprising applying one or more hygienic articles according to the invention to one or more patients, each article having a sensing device with a resonant circuit that differ from each other; and transmitting electromagnetic energy to said resonant circuits.

In an embodiment, the method further comprises monitoring at least one response of said resonant circuits, thereby allowing the prior art techniques of interrogating the resonant circuit to be used.

In a preferred embodiment, the method further comprises monitoring changes of the transmission of electromagnetic energy of one or more oscillators transmitting electromagnetic energy to said resonant circuits, thereby obtaining the advantages of the method according to .the present invention.

Further advantages will be apparent from the description.

Sensing Devices

In its broadest aspect, the sensing device according to the present invention does not necessarily depend on the method of detecting changes of one or more characteristics of the resonant circuit, i.e. for example by detecting the change of the transmission of electromagnetic energy of the oscillators according to the invention, or by detecting a response of the resonant circuit according to prior art methods. However, the specific resonant circuit used typically depends on the parameter to be detected, e.g. fluid or temperature.

Known methods include those referenced in U.S. Pat. No. 4,646,066, e.g. U.S. Pat. No. 4,321,586.

According to the aspect of the invention relating to detecting a fluid, a resonant circuit has one or more characteristics which change by contact between the resonant circuit and a fluid.

According to the other aspect of the invention relating to detecting a temperature or a temperature difference, a resonant circuit has one or more characteristics which change by exposing the resonant circuit to different temperatures.

In a preferred embodiment of both aspects, the characteristics comprises resistance, capacity, inductance, or any derivative thereof.

By contact of the resonant circuit with the fluid, or by exposing the resonant circuit to different temperatures, one or more of the characteristics resistance R, capacitance C and inductance L, or any derivative thereof, e.g. the resonance frequency $\omega_o=(LC)^{-1_2}$, or higher harmonics thereof, or the quality factor $Q=\omega L/R$, e.g. at resonance $\omega=\omega_o$, change.

When one or more of the characteristics change, the ability of the resonant circuit to receive electromagnetic energy changes. This can be detected by detecting changes in one or more characteristics of one or more oscillators transmitting electromagnetic energy to said resonant circuit.

Generally, sensing devices can be manufactured in any suitable way that allow the external parameters to affect the impedance of the respective resonant circuits.

In the particular aspect of the invention relating to detecting a fluid, resonant circuits can be prepared in any suitable way that ensures the penetration of fluid into the resonant circuit to such an extent that one or more of its characteristics are changed.

In the particular aspect of the method of detecting a fluid, the. change of characteristics of the resonant circuit causes a detectable change in one or more of the characteristics of the one or more oscillators.

In a preferred embodiment, the resonant circuit consists of a coil having separated windings which can receive the fluid and short cut the circuit.

The windings can be of any suitable material. In a preferred embodiment, the windings are made of an electrically conducting material selected from the group consisting of metals such as aluminium, copper, tin; an electrically conducting polymer such as polyaniline; and an electrically conducting polymer blend such as poly(p-phenylene vinylene), polyacrylamide, polyaniline and polyethylene, or combinations of these.

Specifically useful electric conducting polymers include a flexible, crease resistant, one component, carbon filled ink and coating sold by Emerson & Cuming Speciality Polymers under the trademark Amicon C 932-74. Another useful electric conducting polymer is a higly flexible, crease resistant, one component, silver filled, ink and coating sold by Wacker Chemikemi under the trademark Elastosil N 189. Both products are environmentally acceptable.

In the particularly aspect of detecting temperature changes, the resonant circuits can be prepared in any suitable way that ensures the influence of different temperatures to affect the impedance of the resonant circuit to such an extent that one or more of its characteristics are changed.

In the particular aspect of the method of detecting a temperature change, the change of the characteristics of the resonant circuit causes a detectable change in one or more of the characteristics of the one or more oscillators.

In a preferred embodiment, the resonant circuit consists of a coil having separated windings of which the resistance, inductance, or both, are sensitive to temperature.

The windings can be of any suitable material. In a preferred embodiment, the windings are made of a temperature sensitive, electrically conducting material.

In another preferred embodiment, the coil has to parts serially connected through a temperature sensitive resistance.

The fluid sensing device can be placed in. any suitable position to detect the desired fluid. In preferred embodiments, the fluid sensing device is contained in or attached onto a container; or it is embedded in a diaper; or it is embedded in a carrier with an adhesive, such as a sticker, to be attached on a desired location, e.g. onto said container or diaper.

Several resonant circuits can be positioned in one location to encode for given patterns of frequencies, e.g. several small resonant circuits of e.g. different frequencies placed in a diaper can provide a unique identification of e.g. individual patients or elderly being monitored in a hospital or a nursing home.

Oscillators

According to the invention an oscillator operates in functional proximity of a resonant circuit.

In the present context the expression "functional proximity of a resonant circuit" is intended to mean that an oscillator in one location radiates electromagnetic energy, e.g. in form of radiowaves or microwaves, which can be fully or partly transferred to a resonant circuit in another location.

Generally, any suitable oscillator can be used, i.e. an oscillator which is able to produce electromagnetic oscillations and to emit electromagnetic energy e.g. in form of radiowaves or microwaves which is fully or partly received by the resonant circuit.

It should be understood that more than one oscillator can operate in functional proximity of said resonant circuits e.g. if more oscillators operates at different frequency ranges, and if changes in different characteristics of the resonant circuit are to be detected.

Generally, an oscillator comprises an generator which generates a high frequency signal of radiant energy e.g. an ac current or voltage, or an impulse, of a frequency around that of the resonant circuit. Generators can be any suitable generator known in the art, e.g. radio frequency signal. generators.

In a preferred embodiment, the oscillator comprises a generator generating a signal of electromagnetic energy of a frequency around that of the resonant circuit.

An oscillator comprises one or more inductors. The inductors can be internal or external to a cabinet housing the oscillator. Preferably there is one or more inductors for each different bands of operation for each resonant circuit. Preferably more inductors can be interchanged either manually or automatically. The inductors can be of any suitable form. In a preferred embodiment the inductors are external inductors in form coils.

Functional proximity between the oscillators and the resonant circuits can be achieved in any suitable way. In a preferred embodiment, the inductors are external inductors in form of coils which surrounds the resonant circuit. In a particularly preferred embodiment, the coils are embedded in a bed for monitoring leak of body fluids of a human.

In another preferred embodiment, the oscillators comprises one or more antennas whereby the direction of the electromagnetic, radiation, e.g. radio waves, can be more accurately defined. An antenna can be any suitable antenna known in the art, e.g. a dipole. In a preferred embodiment, the antenna comprises a radiator element, transmission lines, and optional transformers, coupled to the inductor, or constituting a part of the inductor.

Detectors

The apparatus further comprises one or more detectors for detecting one or more changes in one or more characteristics of said oscillators upon changes in the characteristics of one or more resonant circuits.

The characteristics of the oscillators comprise any suitable characteristic.

In a preferred embodiment the characteristics of the oscillator comprise current, voltage, or a derivative thereof such as power, whereby one or more characteristics, or derivatives thereof, of the resonant circuit are detected, e.g. change in frequency, particularly the resonance frequency; change in quality factor; and wholly or partial suppression or restoration of any of these.

In a preferred embodiment one or more of the detectors detect an increase or a decrease of energy loss of one or more of the oscillators.

Further, preferred uses appear from the following detailed description.

BRIEF DESCRIPTION OF THE DRAWINGS

In the following, the invention is further disclosed with detailed description of preferred embodiments, reference being made to the drawings in which

FIGS. 2A–2J show preferred embodiments of a resonant circuit and its production;

FIGS. 3A–3E show other preferred embodiments of a resonant circuit;

FIGS. 9A, 9B, 10A, 10B, 11, and 12A and 12B show typical applications of the method and apparatus according to the invention;

DETAILED DESCRIPTION

Figure 1:
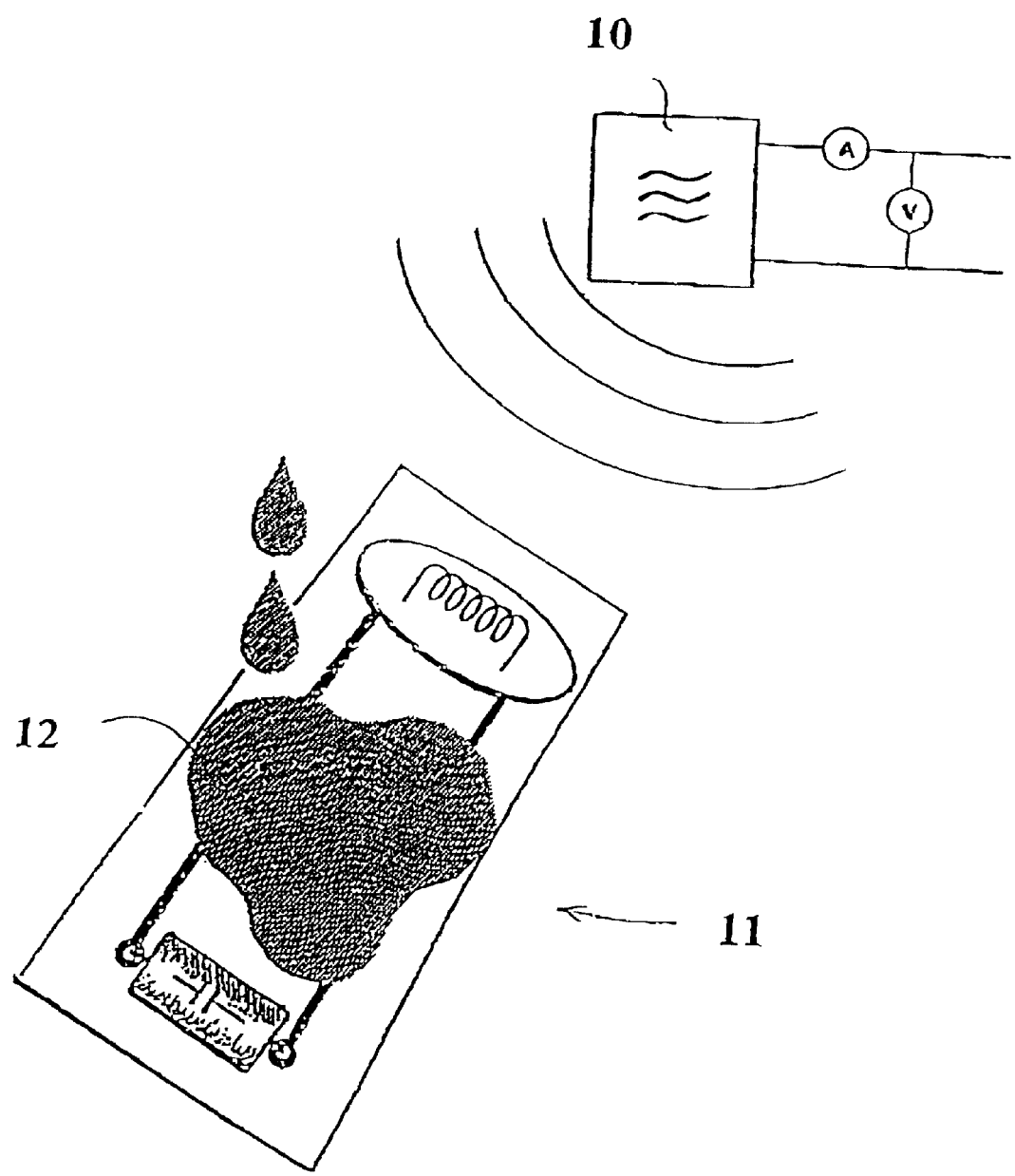
FIG. 1 shows a diagrammatic sketch of the principle of the invention.

FIG. 1 shows a diagrammatic sketch of the principle of the invention.

An oscillator 10, shown in a schematic diagram, emits electromagnetic radiation of a frequency close to that of a resonant circuit 11 located within a functional distance of the oscillator so that a part of the emitted electromagnetic radiation is received by the resonant circuit.

The oscillator provides an output power which ensures that a suitable amount of the radiation is absorbed by the resonant circuit.

A fluid 12 gets in contact with the resonant circuit 11 thereby destroying or disturbing the ability of the resonant circuit to receive electromagnetic energy of the oscillating frequency. Consequently, the oscillator output power changes which is detected by a suitable detection circuit e.g. as schematically shown in the right part of the circuit with measurement of current A and voltage V. The circuit is further connected to power supply and further electronics (not shown).

FIGS. 2A–2D show preferred embodiments of a resonant circuit, in particular for a sensing device according to the invention.

FIG. 2A shows a resonant circuit produced by providing an electrical conductor, i.e. electrical conducting means, e.g. a metallic conductor such as aluminium or an electrically conducting coating, in form of two serially connected coils 21, 22 terminating in plates 24,25 or. a substrate 23, e.g. a textile, a paper, or a. suitable plastic foil. The substrate is folded along the line A—A, as shown in FIG. 2B, providing the back surfaces of the substrate against each other and the front surfaces of the substrate carrying the coil away from each other. Thereby the formation of short circuits between the coils is avoided as further shown in the folded substrate in FIGS. 2C and 2D.

Depending on the degree of folding, the distance between the plates 24,25 is changed, thereby providing a variable capacitance.

It should be noted that the skilled person can select the number of windings and their directions with respect to each other, for either enhancing coupling or decoupling of the magnetic fields of the coils of the folded substrate.

FIG. 2D shows a cross section view of the resonant circuit along the line B—B in FIG. 2C together with an equivalence diagram of the resonant circuit. The two serially connected coils 21, 22 project from each side of the folded substrate 23. The two center areas 24, 25 of the coils make up the plates of a capacitor which capacitatively connects the plates of the two coils, thereby providing a resonant L-C circuit, a so-called LC resonant tank circuit. In practice such a circuit will include a resistance R, either in series or in parallel therewith.

This embodiment of the resonant circuit has the advantage of providing exposed coils which are very sensitive to external affects. This is particularly important when the resonant circuit is built in a container or carrier which otherwise protects the coils from external damage.

Figure 2F:
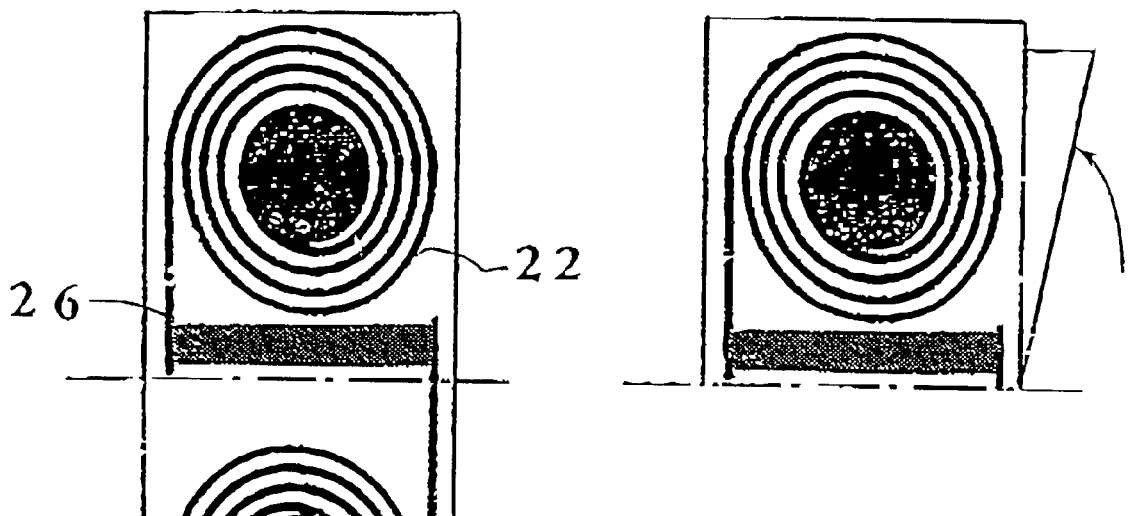
Figure 2E:
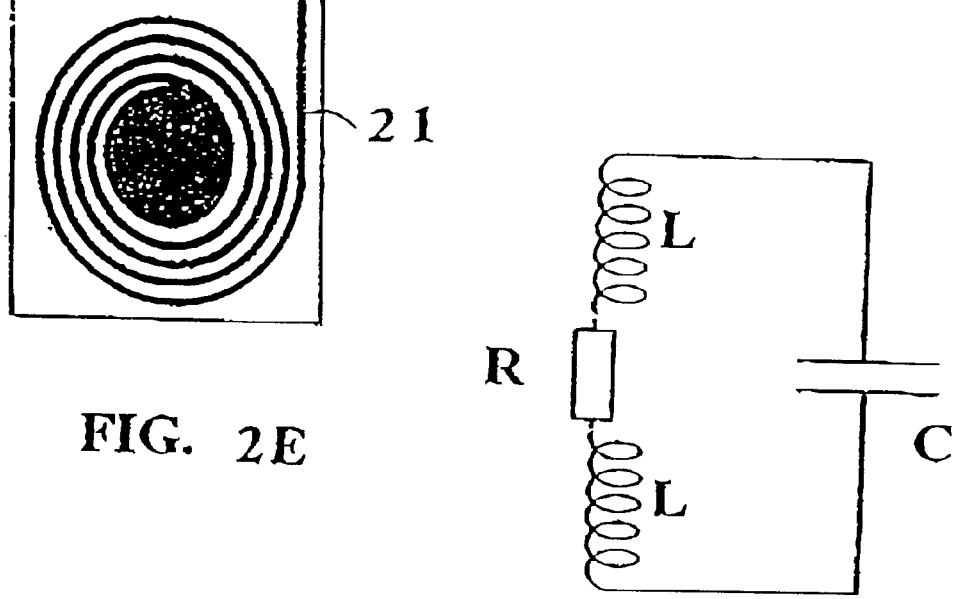

FIGS. 2E and 2F are similar to FIG. 2A and 2B except that a resistance, in particular a temperature sensitive resistance, 26 has been inserted between the coils 21,22.

Figure 2G:
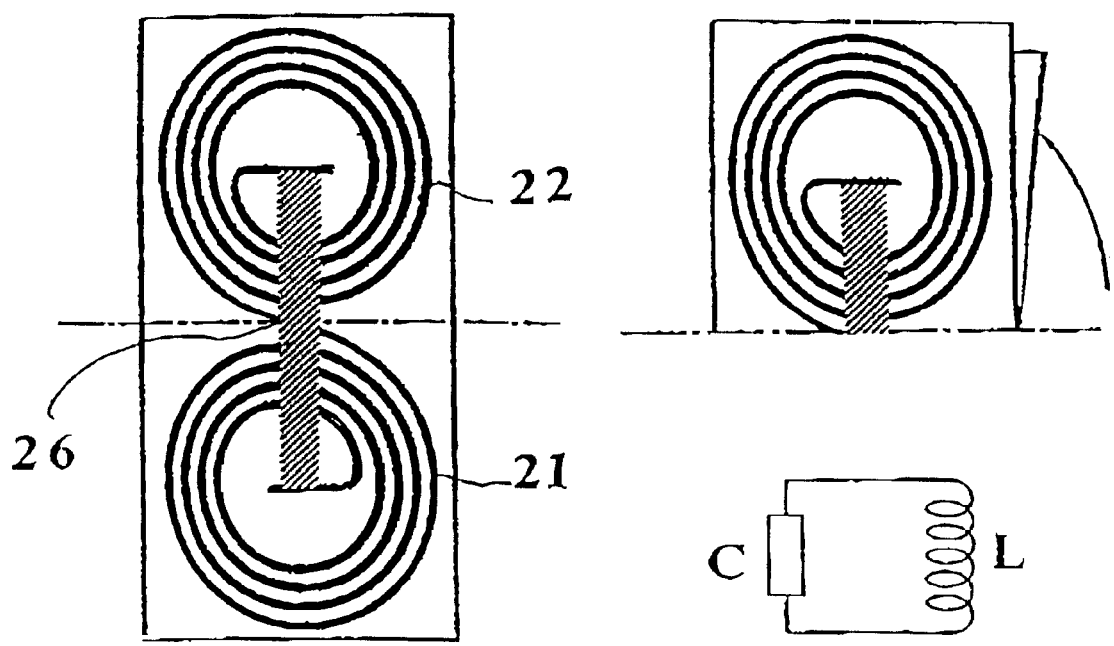
Figure 2H:
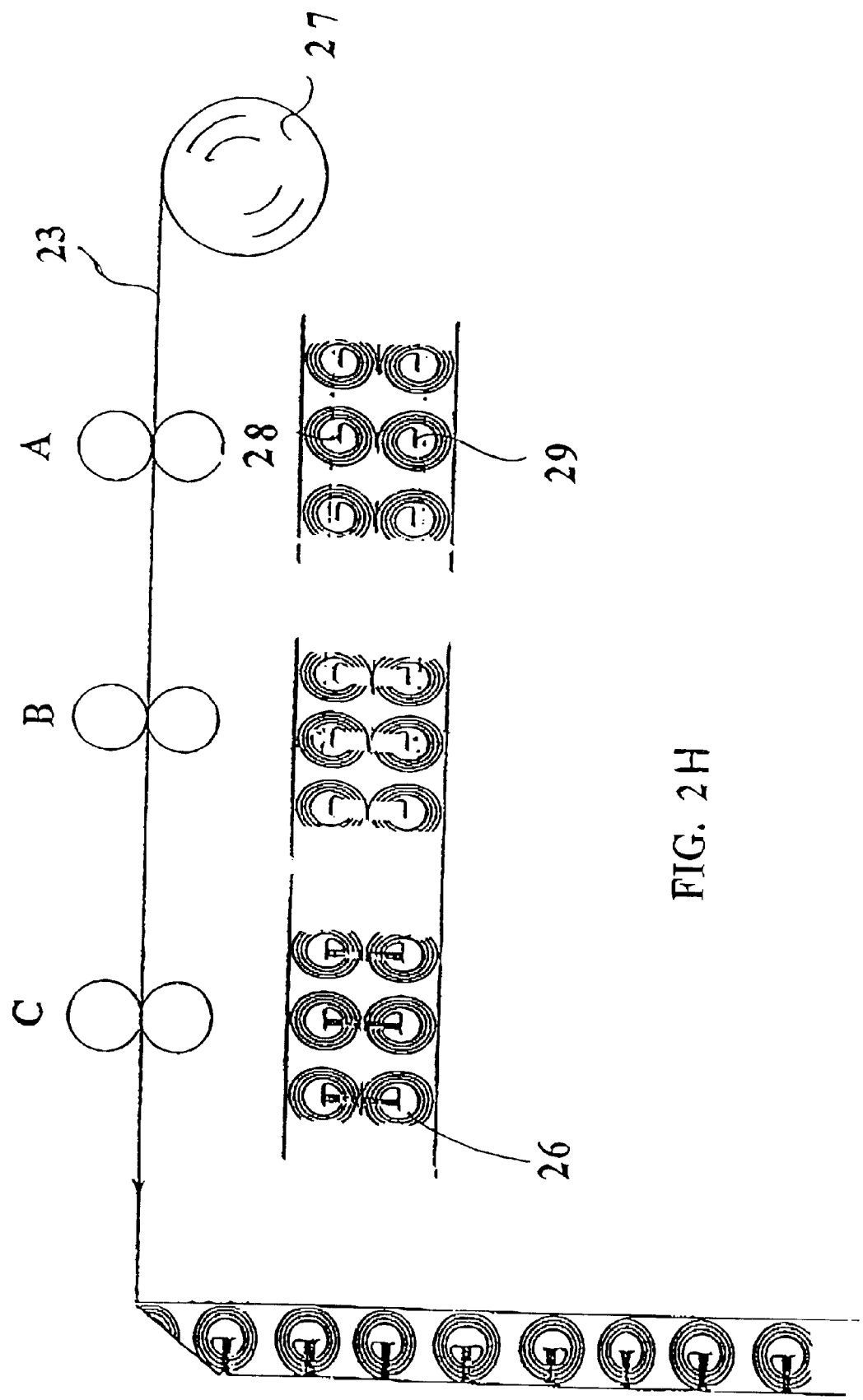

FIG. 2H shows a substrate 23 supplied from a drum 27 to three sets A, B, C of rotational impression drums.

Drum set A applies the coils 21,22 (see FIG. 2G) to the substrate. Drum set B applies an insulating material exposing free coil terminations 28,29, and drum set C applies the resistance 26, e.g. a temperature sensitive material, in parallel with the coils. To the left of FIG. 2H there is shown a folding operation step.

Figure 2I:
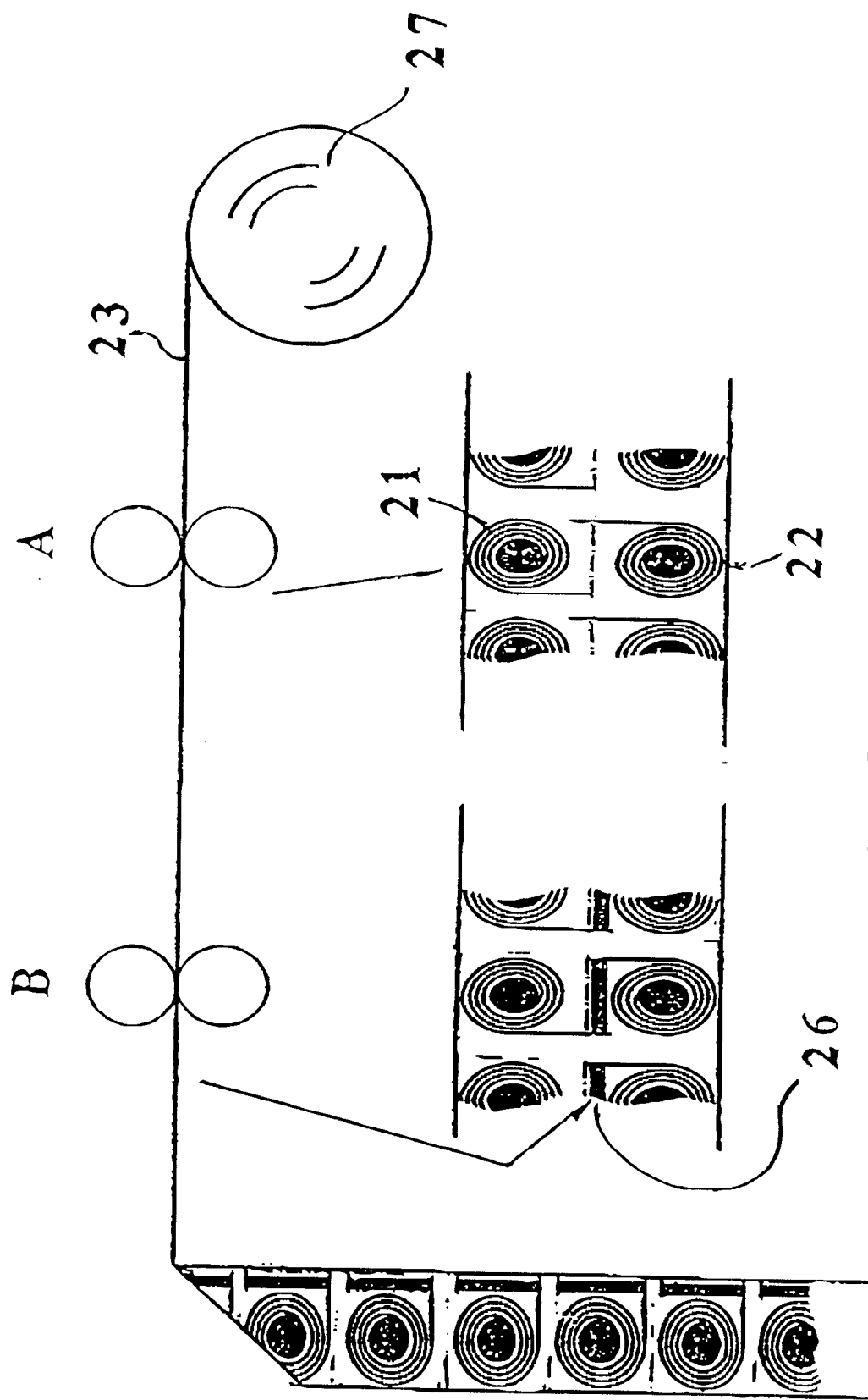

FIG. 2I shows a substrate 23 supplied from a drum 27 to two sets A and B of rotation impression drums. Drum set A applies coils 21,22 to the substrate (see FIG. 2E). Drum set B applies the resistance 26 in series with the coils.

Figure 2J:
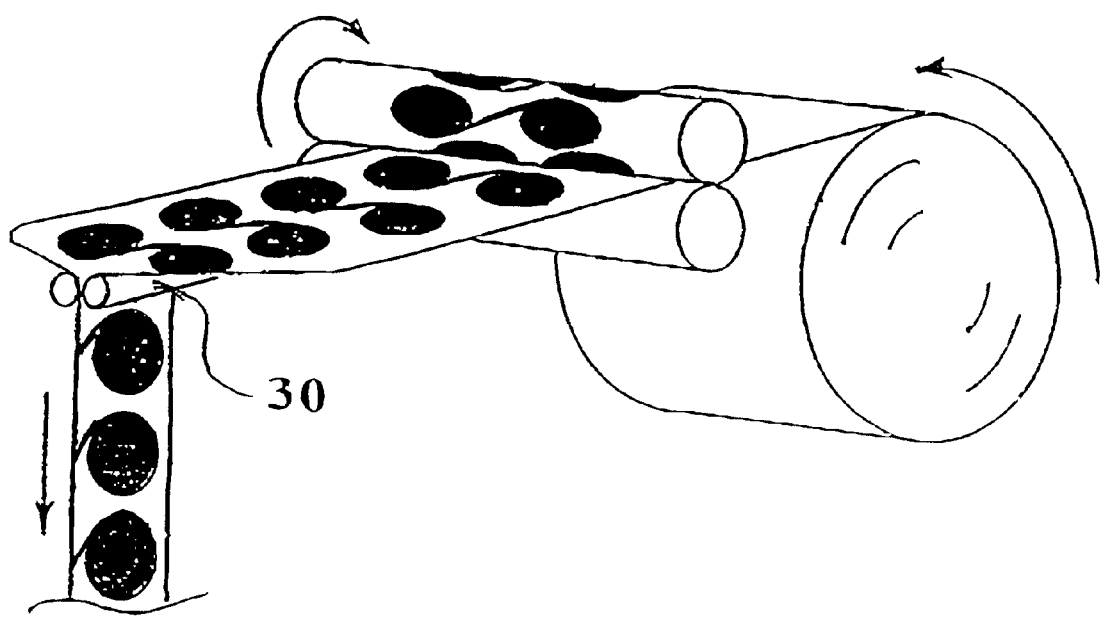

FIG. 2J shows an embodiment of the folding process step.

FIG. 3A is similar to FIG. 2A, except for the direction of folding and insertion of a spacer.

FIG. 3B shows another resonant circuit in which the substrate is folded in the opposite direction of that shown in FIG. 2A, and. in which a spacer 26 of a suitable insulating material, e.g. a textile, a paper, or a suitable plastic, is provided in between the folded parts as shown in FIG. 3C. The center areas 24, 25 make up the plates of a capacitor which are capacitatively connected as shown in FIGS. 3D and 3E.

The spacer may contain a coil correcting metallic conductor.

An advantage of this embodiment is that the coils are better protected against accidental damage, which is useful when the resonant circuit is carried by e.g. a sticker.

Further, the spacer can be designed to have specific fluid penetration properties, e.g. built-in fluid channels which allow an easy access of the fluid to affect the characteristics of the resonant circuit, e.g. the capacitance. Also, the spacer can be a carrier with suitable mechanical properties, e.g. to function as a construction material.

FIG. 4A–4D show different embodiments of the resonant circuit.

Figures 4A, 4B:
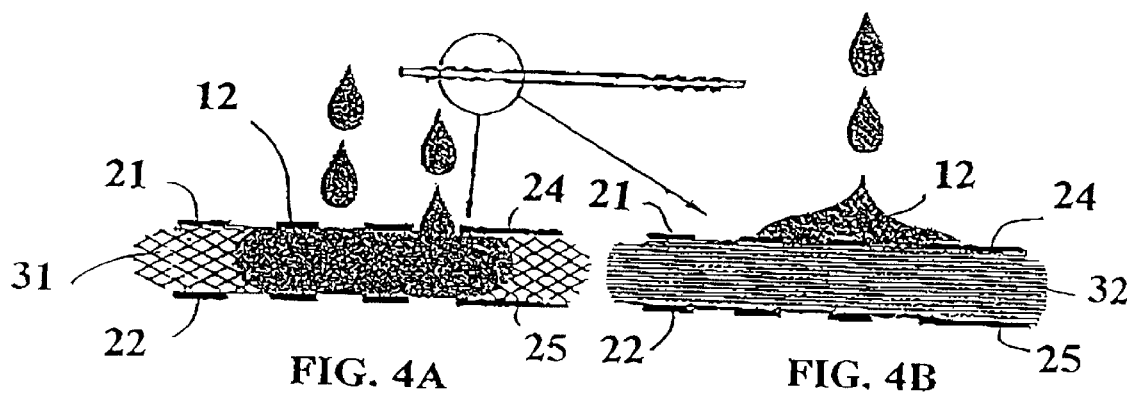
FIGS. 4A–4D show different embodiments of the resonant circuit.

FIGS. 4A shows an embodiment wherein a material 31 between two coils 21, 22, e.g. the substrate 23 shown in FIGS. 2A–2D or the spacer 26 shown in FIG. 3D–3E, is able to absorb the fluid 12 which especially affects the capacitance of the resonant circuit 11. This embodiment is e.g. for uses wherein the fluid substantially changes the dielectric constant of the material between the coil windings 21, 22 and/or plates 24, 25, or the leakage resistance therebetween, e.g. when the fluid is a liquid such as water or urine, or e.g. an organic solvent or oil; or when the fluid is a gas. which differ from that which is present in the resonant circuit, e.g. air.

Figures 4C, 4D:
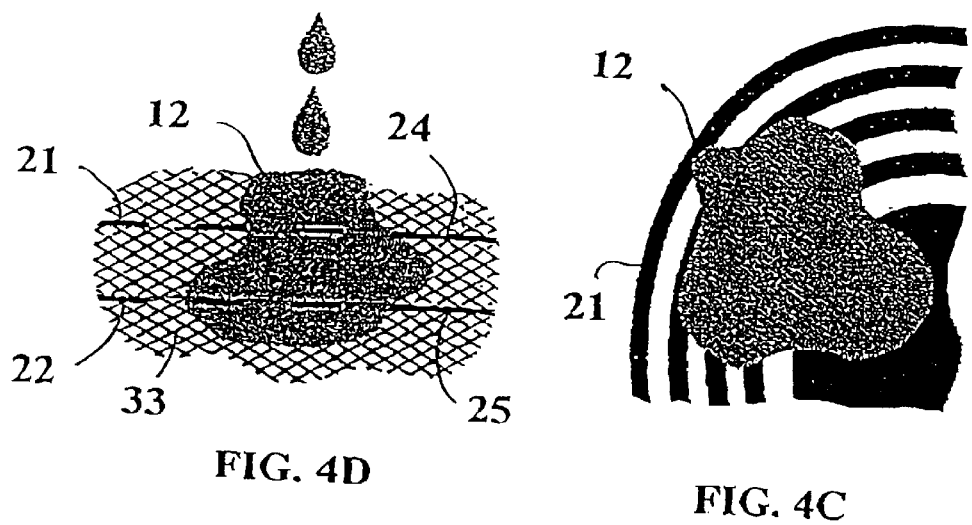

FIG. 4B shows another embodiment wherein the material 32 between the two coils 21, 22 is not absorbing the fluid, whereby especially the conductance between the windings of the coil is affected. FIG. 4C shows a top view thereof. This embodiment is e.g. for uses wherein the fluid is an electrically conducting fluid such as an electrolyte.

FIG. 4D shows another embodiment wherein the coil windings 21, 22 are embedded in a fluid absorbing environment 33.

Figure 5:
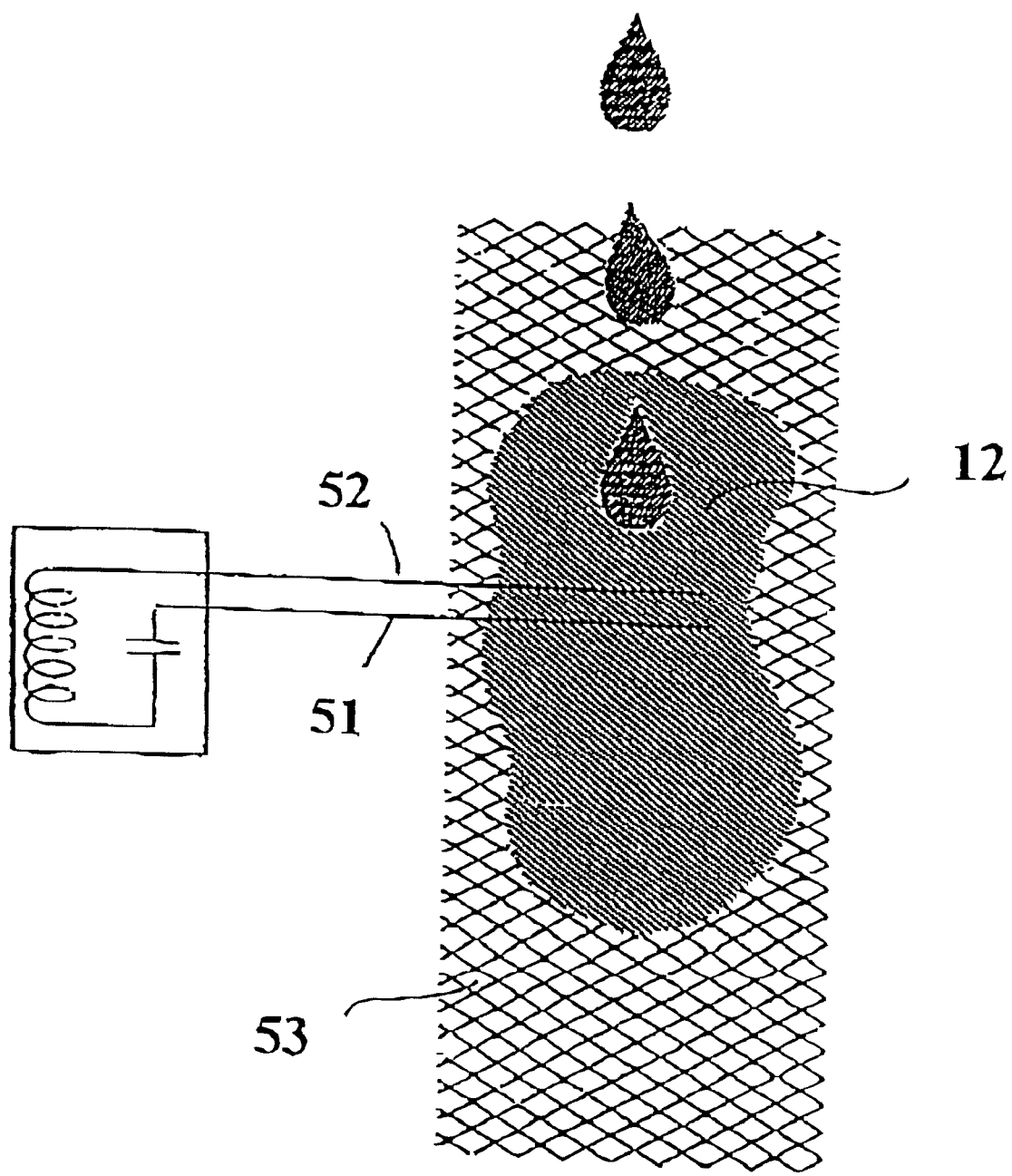
FIG. 5 shows another preferred embodiment wherein the operation of the resonant circuit depends on the presence of an electric conducting fluid.

FIG. 5 shows another embodiment of the resonant circuit wherein the resonant circuit comprises two conductors located in a fluid absorbing material 53. Originally, the two conductors are not connected. When the fluid absorbing material 53 absorbs sufficient electric conducting fluid 12, or a fluid which affects the leak current between the two conductors, the resonant circuit becomes able to resonate and receive electromagnetic energy from the oscillator.

FIGS. 6, 7, and 8A and 8B show different embodiments of applications of the resonant circuit, in particular for a sensing device according to the present invention.

Figure 6:
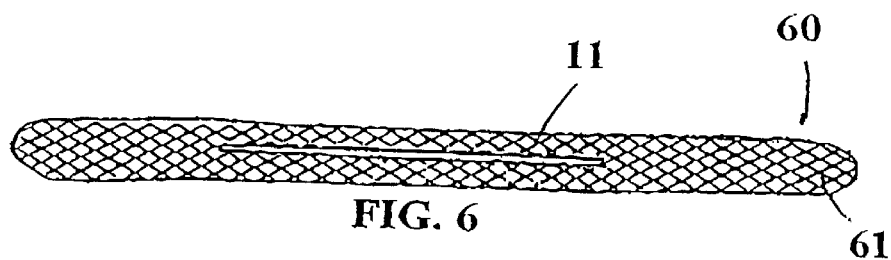
FIGS. 6, 7, and 8A and 8B show different embodiments of applications of the resonant circuit.

FIG. 6 shows a resonant circuit 11 embedded in a diaper or bandage 60 able to absorb the fluid, e.g. urine or a body fluid, e.g. blood from a wound, by an absorbing material 61.

Figure 7:
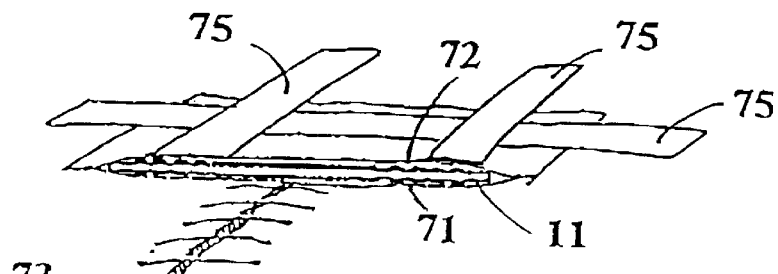

FIG. 7 shows a laminated resonant circuit 11 having the resonant circuit 11 embedded, between two materials 71, 72 of which one 71 is compatible with human skin and allows humidity and body fluid to penetrate. The laminated circuit can be applied directly on the skin wholly or partly covering a bleeding wound 73. It can be fixed to the skin either by means of a plaster or a tape 75.

Figure 8:
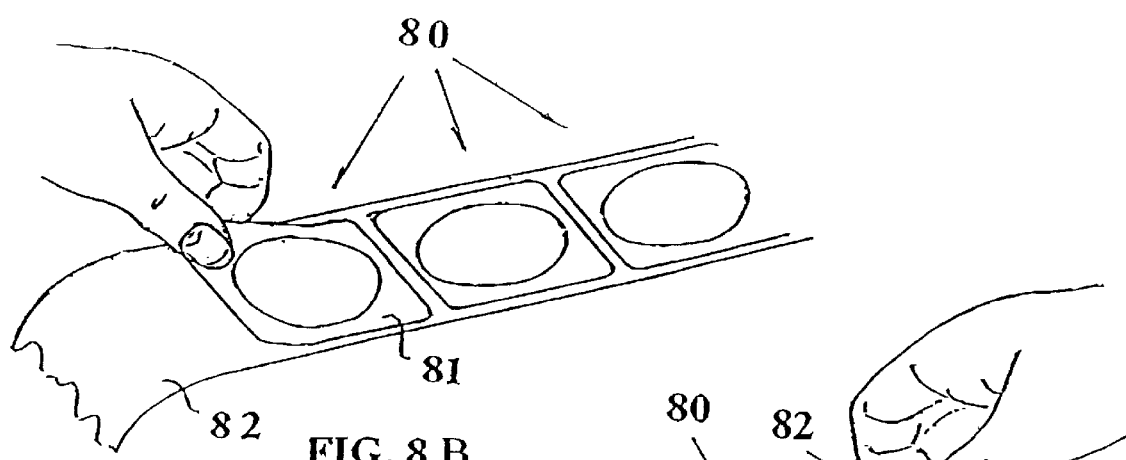
Figure 8:
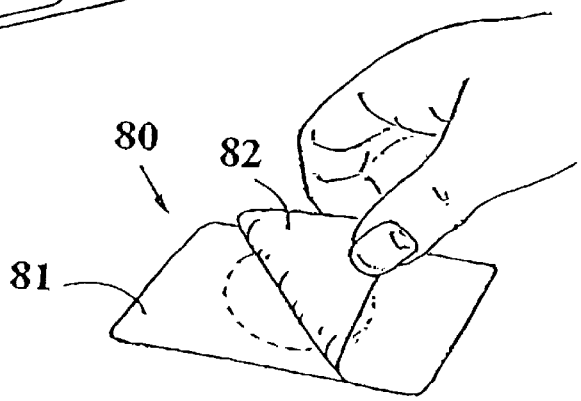

FIG. 8A shows an attachable resonant circuit 80 of the type shown in FIG. 7 wherein the resonant circuit is embedded between a carrier material wholly or partly covered with adhesive, e.g. a skin compatible adhesive, material 81 for affixing the resonant circuit to e.g. the skin, or a diaper, and a releasable cover material 82 covering said adhesive and to be removed without destroying the adhesive properties thereof before use. It should be noted that the resonant circuit can be of the laminated type, or it can be directly adhered to or incorporated in the carrier material.

FIG. 8B shows several attachable resonant circuits 80 similar to that of FIG. 8A provided on an "endless" releasably cover material 81, particularly useful for fast and easy handling and application of many sensing devices, e.g. fluid or temperature, to a human body or an article, e.g. a diaper.

Figure 9A:
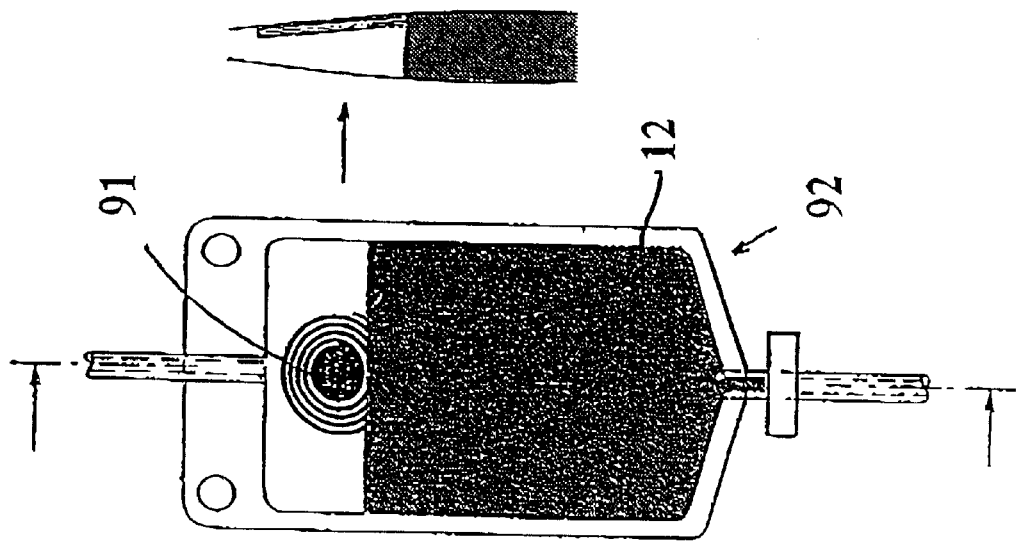
Figure 9B:
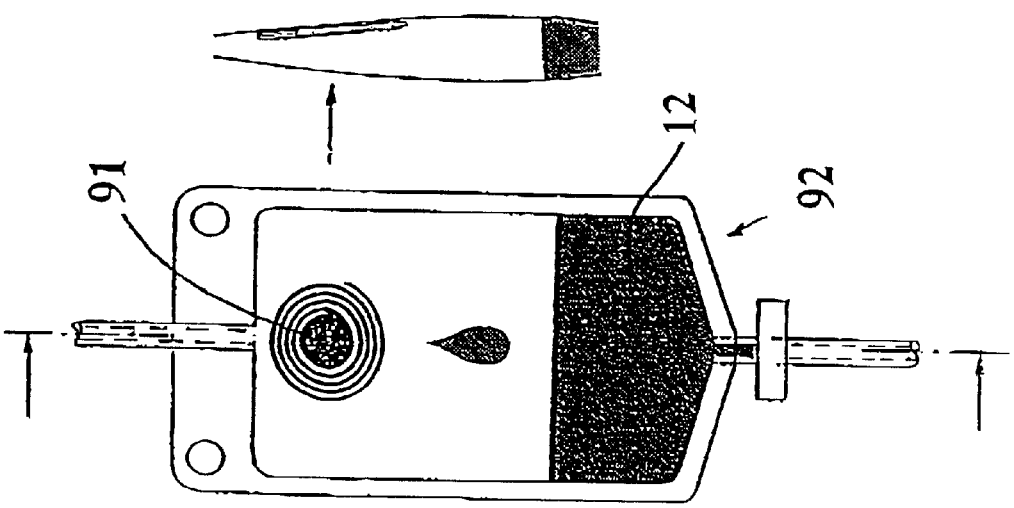

FIGS. 9A and 9B with cross sectional views show application of a fluid sensing device, i.e. a resonant circuit 91 e.g. of the type shown in FIG. 4B or FIG. 7, contained in a container 92, e.g. a collection bag, or drain bag, for monitoring the level of the collected fluid, e.g. drain fluid 12. The characteristics of the resonant circuit is changed upon contact with the fluid, see FIG. 9B.

FIGS. 10A and 10B show another application of a resonant circuit 101, e.g. of the type shown in FIGS. 3A–3E, attached to the outside of a container 102, e.g. an infusion bag, at the fluid level A—A for monitoring the level of a fluid 12 contained therein, when the level of the fluid sinks below the level A—A, the ability of the resonant circuit to receive electromagnetic energy from an oscillator changes because the capacitor between the serially connected coils changes as the container sides collapses against each other. This embodiment can be used to monitor infusion liquids and indicate an alarm, when the infusion bag is empty.

Figure 11:
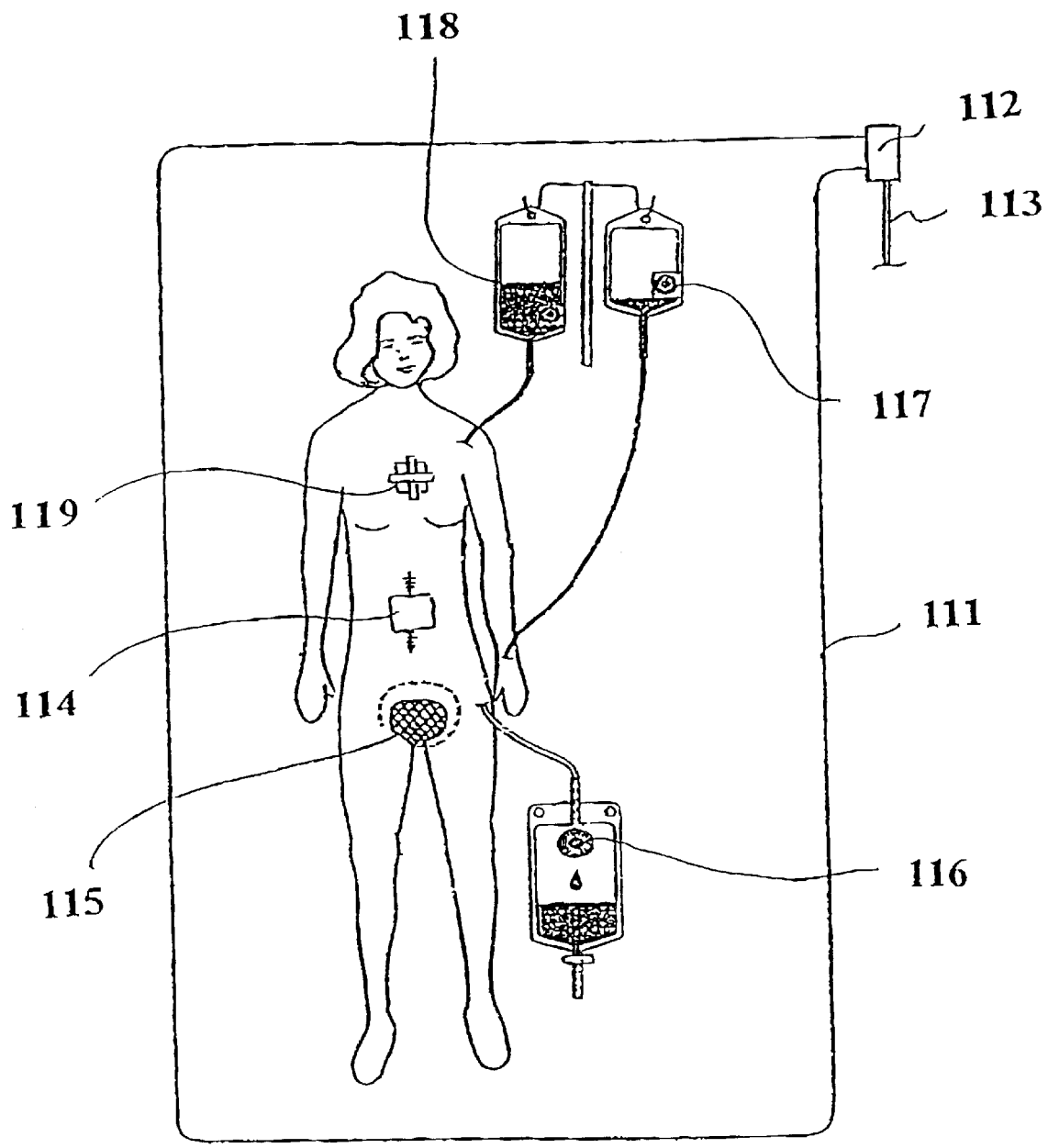

FIG. 11 shows typical applications of the method and apparatus according to the invention.

A human is positioned within an external inductor 111 of the oscillator 112 which is powered externally and electronically communicating with external electronics through electrical connections 113, e.g. power cables and/or communication lines.

A resonant circuit 114 e.g. of the type shown in FIG. 7 is partly covering a wound which may leak body fluid.

A resonant circuit 115 e.g. of the type being embedded in a diaper shown in FIG. 6 is placed to monitor a leak of body fluid such as incontinence urine or faeces.

Further, a resonant circuit 116 is applied in a fluid level detector of a collected body fluid from a drain.

Also, resonant circuits 117 and 118 are applied in two infusion containers for monitoring when they are empty.

Finally, resonant circuit 119, a temperature sensor, is applied to the body.

FIG. 12A shows a similar arrangement of resonant circuits as in FIG. 11 wherein the external inductor 111 is exchanged with an antenna 121.

In FIG. 12B a walking patient who is being monitored for fluid and temperature according to the invention is illustrated.

If all four applications of the resonant circuits are being applied at the same location as shown in FIGS. 11 and 12, then the characteristics of the resonant circuits are chosen to provide different responses for the individual resonant circuits, e.g. different resonance frequencies, so that the risk of false interpretation of the oscillator characteristics is avoided or minimized.

Figure 13:
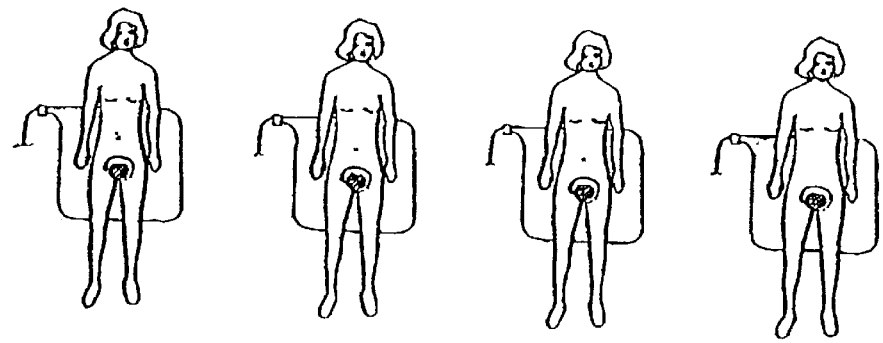
FIGS. 13, 14, and 15 show different configurations of the external inductor of the oscillator and an antenna.
Figure 14:
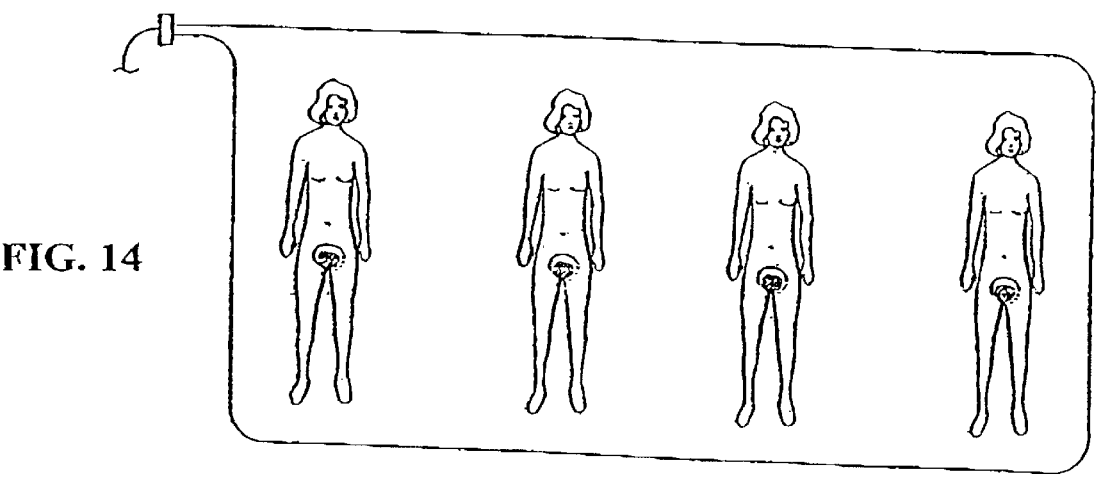
Figure 15:
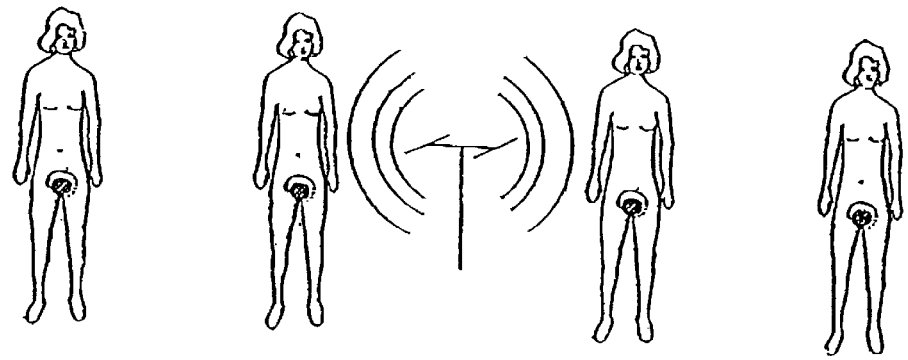

FIGS. 13, 14, and 15 show different configurations of the external inductor of the oscillator for uses of the resonant circuits in several locations. For simplicity, the uses of resonant circuits as level detectors, empty infusion container detector, bleeding detectors, etc. are not shown.

In FIG. 13 there is one oscillator/external inductor and one resonant circuit or optionally a set of more resonant circuits for each location, e.g. for, each patient.

In FIG. 14, there is one oscillator/external inductor, but several resonant circuits for several locations. This application presumes e.g. different resonance frequencies or patterns of frequencies for the different resonant circuits.

In FIG. 15, there is one oscillator, the inductor of which is connected to an antenna. This application presumes e.g. different resonance frequencies or patterns of frequencies for different circuits. It provides the possibility that patients can move around more freely as they are not bound to a certain confirmed area as that shown in FIG. 14.

Combinations of these configurations are particularly preferred. In particular, consideration of radio frequencies available and allowed at the site of application may exclude application of an antenna in order to limit any undesired interference with radiowave sensitive equipment.

A particularly preferred combination consists in combining the configurations. FIG. 13 and FIG. 14 which is particular useful in situations where typically elderly people are being monitored in hospitals or nursing homes. In these applications, some patients or elderly are lying in bed and. some walk around in confined areas. However, both of these categories of patients or elderly can be supervised from a central monitoring facility.

Thus, e.g. elderly can be supervised for a leak of body fluid and taken care of by proper action, e.g. replacement of a diaper, which considerably improves their well-being and comfort.

Figure 16:
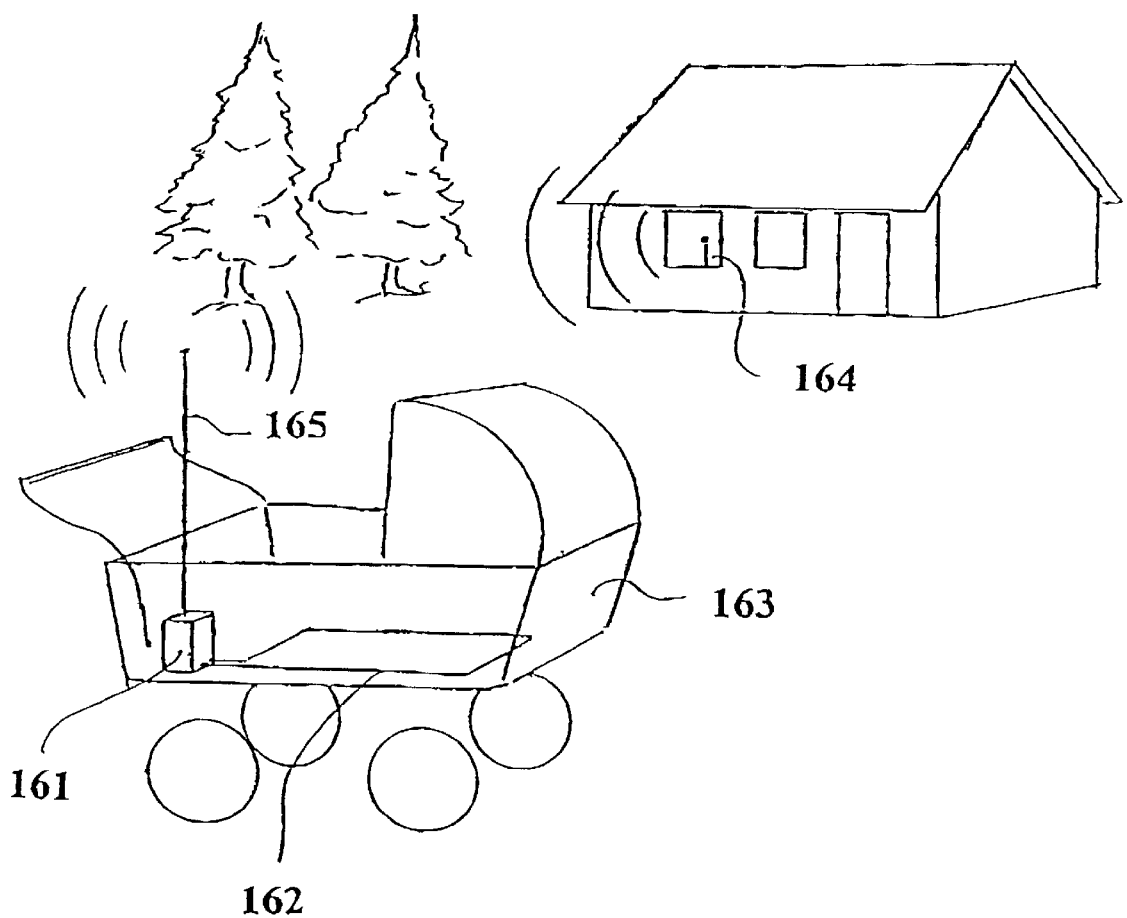
FIG. 16 shows a typical application for remote monitoring of baby wetness in a baby carriage.

FIG. 16 shows a particular application where the resonant circuit is typically embedded in a diaper for babies put to sleep in a baby carriage. The oscillator 161 typically has an external inductor 162 arranged to a remote transmitter/receiver 164, 165.

Alternatively, if the baby carriage does not provide an electromagnetic shielding effect, and suitable radio frequencies are available, the oscillator can be remotely placed and wireless sensing the characteristics of the resonant circuit in the diaper and detecting whether the diaper has reached its level of discomfort.

What is claimed is:

1. A method of detecting a fluid, said method comprising:
   providing one or more oscillators transmitting electromagnetic energy;
   providing one or more resonant circuits for receiving electromagnetic energy from the oscillators;
   bringing the fluid and the one or more resonant circuits into contact with each other so that the reception of electromagnetic energy of the resonant circuits are changed; and
   detecting changes of the transmissions of electromagnetic energy of the oscillators by changes in one or more characteristics thereof upon the changes in the receptions of the electromagnetic energy of the resonant circuits, wherein the step of providing one or more resonant circuits comprises providing a substrate having a back side and a front side, and at least one electrical conducting means, comprising an inductance (L), positioned on or embedded in said back side, front side, or both, of the substrate;

said substrate further having at least two parts in a mutual overlaying relationship, so that said conducting means together with at least a part of the substrate provides a capacitance (C); said inductance and capacitance being electrically connected to form a resonant circuit; and said conducting means being exposed to the fluid to affect a parameter of said resonant circuit.

2. A method according to claim 1 wherein the one or more resonant circuits includes a resistance component (R) contact between the fluid and the one or more resonant circuits changes one or more characteristics of the resonant circuit comprising resistance (R), capacity (C), inductance (L), or any derivative thereof.

3. A body fluid sensor for use with an absorbing article suitable for being worn by a human or animal user and for absorbing body fluids from the human or animal user, the body fluid sensor being suitable for being in close proximity with the absorbing article when worn by the user, the body fluid sensor comprising:

an electrical resonance circuit exclusively of linear elements, the linear elements comprising an inductive element and a capacitive element, electrically coupled to form the electrical resonance circuit responsive to electromagnetic energy, the resonance circuit being accessible by fluids in said absorbing article external to the fluid sensor, the resonance circuit being active as a resonance circuit when an element thereof is accessed by a body fluid and having resonance circuit parameters that change when the resonance circuit is contacted by body fluid in said absorbing article; and wherein said inductive element comprises a flat substrate and a pair of flat coils, the substrate having two layers thereof folded on itself with the coils in an overlaying relationship and said capacitive element formed by the space between the coils.

4. A body fluid sensor according to claim 3, wherein said coils are exposed.

5. A body fluid sensor according to claim 3, wherein said coils are situated with two layers of said substrate therebetween.

6. A body fluid sensor according to claim 3 further comprising an absorbing material capable of absorbing body fluid.

7. A body fluid sensor according to claim 3 wherein said resonance circuit parameters are selected from the group consisting of resistance, capacitance, inductance, dielectric constant, resonance frequency, and quality factor.

8. A device for sensing the presence of body fluid comprising:

an absorbing article suitable for being worn by a human or animal user and to absorb body fluids from the human or animal user; and a body fluid sensor including an electrical resonance circuit exclusively of linear elements, the linear elements comprising an inductive element and a capacitive element, which are electrically coupled to form the electrical resonance circuit responsive to electromagnetic energy, the resonance circuit being accessible by fluids absorbed by said absorbing article, the resonance circuit being active as a resonance circuit when an element thereof is accessed by a body fluid and having resonance circuit parameters that change when the resonance circuit is accessed by a body fluid; and wherein said body fluid sensor includes a flat substrate with at least one flat coil, the substrate having two layers thereof folded on itself with the at least one coil in an overlaying relationship.

9. An absorbing article according to claim 8, wherein said at least one coil is exposed.

10. An absorbing article according to claim 8 wherein said at least one coil is situated between the two folded layers of said substrate.

11. An absorbing article according to claim 8 wherein the body fluid sensor includes an absorbing material capable of absorbing body fluid and said substrate is in contact with said absorbing material.

12. An absorbing article according to claim 8, wherein the parameters of said resonance circuit are selected from the group consisting of resistance, capacitance, inductance, dielectric constant, resonance frequency and quality factor.

13. A system for sensing presence of body fluid in a human, comprising:

a source for transmitting and receiving electromagnetic energy;

means for measuring at least one of the current and voltage of said source;

a body fluid sensor comprising a fluid absorbing material to be worn by a human; and a resonance circuit exclusively of linear elements, the linear elements comprising an inductive element and capacitive element carried by said fluid absorbing article to receive the electromagnetic energy transmitted by said source, the resonance circuit being active as a resonance circuit when an element thereof is accessed by a body fluid and the characteristics of said resonant circuit relative to the electromagnetic energy changing in response to being in contact with fluid absorbed by said fluid absorbing material to change at least one of the current and voltage at said source of electromagnetic energy.

14. A system as in claim 13 wherein said body fluid sensor comprises a flat substrate and at least one flat coil of said resonant circuit thereon.

15. A system as in claim 14 wherein a liquid absorbing material is in contact with said substrate for absorbing body liquids to come into contact with said at least one coil.

16. A system as in claim 14 wherein said at least one coil is exposed.

17. A system as in claim 14 wherein said flat substrate has two layers folded on each other with a space therebetween to form a capacitor with said at least one coil in an overlaying relationship.

* * * * *